US010087160B2

(12) United States Patent
Chheda et al.

(10) Patent No.: US 10,087,160 B2
(45) Date of Patent: Oct. 2, 2018

(54) PROCESS FOR THE MANUFACTURE OF FURURAL AND FURFURAL DERIVATIVES

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 15/502,828

(22) PCT Filed: Aug. 13, 2015

(86) PCT No.: PCT/US2015/044988
§ 371 (c)(1),
(2) Date: Feb. 9, 2017

(87) PCT Pub. No.: WO2016/025677
PCT Pub. Date: Feb. 18, 2016

(65) Prior Publication Data
US 2017/0233361 A1    Aug. 17, 2017

Related U.S. Application Data

(60) Provisional application No. 62/037,209, filed on Aug. 14, 2014.

(51) Int. Cl.
| | |
|---|---|
| *C07D 307/50* | (2006.01) |
| *B01J 21/02* | (2006.01) |
| *B01J 23/02* | (2006.01) |
| *B01J 23/06* | (2006.01) |
| *B01J 23/26* | (2006.01) |
| *B01J 23/34* | (2006.01) |
| *B01J 23/72* | (2006.01) |
| *B01J 23/755* | (2006.01) |
| *C10L 1/18* | (2006.01) |
| *B01J 8/02* | (2006.01) |
| *C10L 1/185* | (2006.01) |

(52) U.S. Cl.
CPC .......... *C07D 307/50* (2013.01); *B01J 8/0278* (2013.01); *B01J 21/02* (2013.01); *B01J 23/02* (2013.01); *B01J 23/06* (2013.01); *B01J 23/26* (2013.01); *B01J 23/34* (2013.01); *B01J 23/72* (2013.01); *B01J 23/755* (2013.01); *C10L 1/18* (2013.01); *B01J 2208/027* (2013.01); *C10L 1/1857* (2013.01)

(58) Field of Classification Search
CPC ......... C07D 307/50; B01J 21/02; B01J 23/02; B01J 23/06; B01J 23/26; B01J 23/34; B01J 23/72; B01J 23/755
See application file for complete search history.

(56) References Cited

U.S. PATENT DOCUMENTS

| | | | |
|---|---|---|---|
| 2,078,241 | A | 4/1937 | Fulmer et al. |
| 2,536,732 | A | 1/1951 | Dunlop |
| 4,409,032 | A | 10/1983 | Paszner et al. |
| 4,461,648 | A | 7/1984 | Foody |
| 4,533,743 | A | 8/1985 | Medeiros et al. |
| 5,820,687 | A | 10/1998 | Farone et al. |
| 8,168,807 | B2 | 5/2012 | Wabnitz et al. |
| 8,466,242 | B2 | 6/2013 | Geremia et al. |
| 2010/0019191 | A1 | 1/2010 | Hoffer et al. |
| 2010/0312028 | A1 | 12/2010 | Olson et al. |
| 2012/0107887 | A1 | 5/2012 | Chheda et al. |
| 2012/0122152 | A1 | 5/2012 | Blackbourn et al. |
| 2012/0157697 | A1 | 6/2012 | Burket et al. |
| 2012/0302765 | A1 | 11/2012 | Dumesic et al. |
| 2013/0295629 | A1 | 11/2013 | Weider et al. |
| 2014/0018555 | A1 | 1/2014 | DeVries et al. |
| 2014/0107355 | A1 | 4/2014 | Dumesic et al. |

FOREIGN PATENT DOCUMENTS

WO    2007009463    1/2007

OTHER PUBLICATIONS

Galbe, et al.; "A review of the production of ethanol from softwood"; Appl. Microbiol. Biotechnol.; vol. 59; pp. 618-628; 2002.
Holtzapple, et al.; The Ammonia Freeze Explosion (AFEX) Process; Applied Biochemistry and Biotechnology; vol. 28/29; pp. 59-74; 1991.
Kumar, et al.; "Methods for Pretreatment of Lignocellulosic Biomass for Efficient Hydrolysis and Biofuel Production"; Ind. Eng. Chem. Res.; vol. 48; pp. 3713-3729; 2009.
Lange, Jean Paul; "Sustainable developement: efficiency and recyling in chemicals manufacturing"; Shell Research & Technology Centre; Amsterdam; Published as an Advance Article on the web Oct. 8, 2002; 5 pages.
Lange, et al.; "Furfural—A Promising Platform for Lignocellulosic Biofuels"; ChemSusChem; vol. 5; pp. 150-166; 2012.
Lavarack, et al.; "The acid hydrolysis of sugarcane bagasse hemicellulose to produce xylose, arabinose, glucose and other products"; Biomass and Bioenergy; vol. 23; pp. 367-380; 2002.
Möller; "Outputs from the EPOBIO project"; published by CPL Press, Tall Gables, The Sydings Speen, Newbury, Berks RG14 TRZ UK; 2006.
Mosier, et al.; "Features of promising technologies for pretreatment of lignocellulosic biomass"; Bioresource Technology; vol. 96; pp. 673-686; 2005.
Ong; "Conversion of Lignocellulosic Biomass to Fuel Ethanol—A Brief Review"; The Planter; vol. 80, No. 941; pp. 517-524; 2004.
Periodic-Table-Literature; "Periodic Table of the Elements"; CRC Handbook of Chemistry and Physics; 2 pages.
Yang et al.; One-Step Catalytic Transformation of Carbohydrates and Cellulosic Biomass to 2,5 Dimethyltetrahydrofuran for Liquid Fuels; ChemSusChem; vol. 3; pp. 597-603; 2010.
SP0486—International Search Report for PCT/US20115/044988 dated Oct. 6, 2015; 4 pages.

Primary Examiner — Timothy R Rozof

(57) ABSTRACT

The present invention provides a process for preparing furfural and furfural derivatives using a furfural-derived solvent.

17 Claims, 1 Drawing Sheet

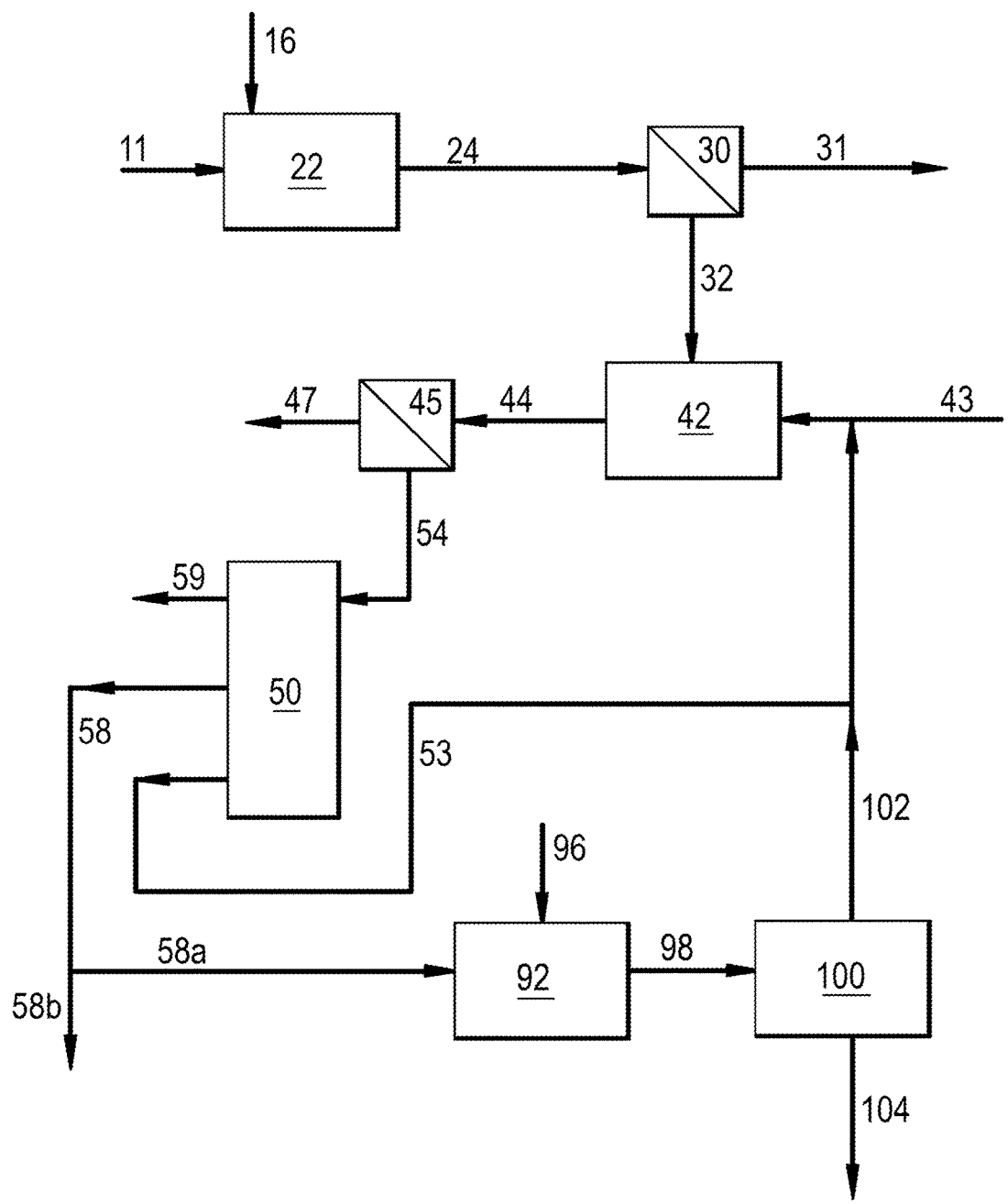

PROCESS FOR THE MANUFACTURE OF FURURAL AND FURFURAL DERIVATIVES

PRIORITY CLAIM

The present application is the National Stage (§ 371) of International Application No. PCT/US2015/044988 filed Aug. 13, 2015, which claims priority from U.S. Patent Application No. 62/037,209, filed Aug. 14, 2014 incorporated herein by reference.

FIELD OF THE INVENTION

The inventions disclosed and taught herein relate generally to novel processes for the preparation of furfural and furfural derivatives from C5 sugars. More specifically, the invention pertains to a process for the conversion of biomass to furfural and furfural derivatives.

BACKGROUND OF THE INVENTION

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. A number of approaches to overcome this recalcitrance have been performed and the breakdown of these polymers into sugars, saccharification, has a long history.

US2014/0018555 describes a process for producing furfural from lignocellulose-comprising biomass is disclosed. The biomass is slurried in water and optionally an acid, subjected to hydrolysis, and then subjected to a solid/liquid separation to yield at least an aqueous fraction comprising C5 and C6 sugars and a solid fraction comprising cellulose and lignin. Furfural is obtained by adding an organic solvent to the aqueous fraction, heating at 120-220° C. for a sufficient time to form furfural, cooling, and separating an organic phase comprising at least part of the furfural from an aqueous phase. As suitable organic solvents water miscible and water immiscible organic solvents are suggested.

The process of US2014/0018555 requires a continuous supply of organic solvent, which is undesired when the process is operated at remote locations.

U.S. Pat. No. 8,168,807 describes a process for a one stage preparation of 2-methyltetrahydrofuran from furfural over two catalyst in a structured bed. The 2-methyltetrahydrofuran is prepared by one-stage hydrogenation of furfural with a hydrogen-comprising gas in the presence of a structured bed of at least one copper catalyst and at least one catalyst which comprises at least one noble metal from groups 8, 9 and/or 10 of the periodic table of the elements applied on a support material. There is a need for improving the efficiency of the process by reducing the demand for organic solvent to be provided to the process.

SUMMARY OF THE INVENTION

It has now been found that make-up amounts of organic solvent may be prepared on site reducing the need to provided organic solvent externally.

Accordingly, the present invention provides a process for preparing furfural and/or furfural derivatives, comprising:
 (a) providing an aqueous $C_5$ sugar-containing feed stream;
 (b) contacting an aqueous phase comprising the aqueous $C_5$ sugar-containing feed stream with an organic phase comprising organic solvent at a temperature in the range of about 100° C. to about 300° C. for a time sufficient to effect a dehydration reaction to convert $C_5$ sugar to furfural, wherein at least part of the furfural dissolves in the organic solvent phase to form a furfural-containing organic phase;
 (c) separating the furfural-containing organic phase from the aqueous phase;
 (d) converting at least part of the furfural to a tetrahydrofuranic derivative to obtain tetrahydrofuranic derivative-containing product; and
 (e) providing at least part of the tetrahydrofuranic derivative to step (b) as organic solvent.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 1 illustrates a schematic process diagram for producing furfural and/or furfural derivatives from biomass in accordance with an embodiment of the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further in this connection, certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar, protein and oil such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like. In some embodiments, the lignocellulosic biomass is selected from the group including, but not limited to, corn stover, straw, bagasse, miscanthus, sorghum residue, switch grass, bamboo, water hyacinth, hardwood, hardwood, softwood, wood chips, and wood pulp.

As used herein, the term "carbohydrate" is defined as a compound that consists only of carbon, hydrogen, and oxygen atoms, wherein the ratio of carbon atoms to hydrogen to oxygen atoms is 1:2:1. Well known examples of carbohydrates include sugars and sugar-derived oligomers and sugar-derived polymers.

As used herein, the term "lignocellulosic" means, comprising cellulose, lignin and hemicellulose and/or pentosan.

As used herein, the term "hemicellulosic" refers to a material comprising $C_5$ and $C_6$ sugar polymers. Hemicellulose consists of short, highly branched chains of sugars. It contains five-carbon sugars (usually D-xylose and L-arabinose) and six-carbon sugars (D-galactose, D-glucose, and D-mannose) and uronic acid. The sugars are partially acetylated. Typically, the acetyl content is 10 to 15 wt %, based on the hemicellulose or 2 to 3 wt %, based on the biomass.

The relative content of $C_5$ versus $C_6$ sugars produced from hemicellulose depends on the source of the hemicellulose. When hydrolyzed, the hemicellulose from hardwoods releases products rich in xylose (a five-carbon sugar). The hemicellulose contained in softwoods, by contrast, yields more six-carbon sugars. The branched nature of hemicellulose renders it amorphous and relatively easy to hydrolyze to its constituent sugars compared to cellulose.

As used herein, the term "2-methyltetrahydrofuran", or "2-Me-THF", refers to the organic compound having the molecular formula $C_5H_{10}O$ and the structure shown below, and includes both enantiomeric forms, either together or separately.

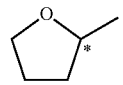

The term "furfural", or "2-furaldehyde", as used herein, refers to the organic compound having the molecular formula $C_5H_4O_2$ and the structure shown below.

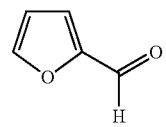

As used herein, the term "miscible" refers to a mixture of components that, when combined, form a single liquid phase (i.e., the mixture is "monophasic") under specified conditions (e.g., component concentrations, temperature).

As used herein, the term "immiscible" refers to a mixture of components that, when combined, form a two, or more, phases under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two separated liquid phases, for example, an aqueous or water-rich phase and an organic or organic solvent-rich phase. The term "biphasic" can also be used to describe a method employing such a reaction medium.

As used herein the term "water-miscible organic solvent" refers to an organic solvent that can form a monophasic solution with water at the temperature and concentration at which the reaction is carried out.

As used herein, the term "immiscible" refers to a mixture of components that, when combined, form a two, or more, phases under specified conditions (e.g., component concentrations, temperature).

Unless otherwise defined, all technical and scientific terms used herein have the same meaning as commonly understood by one of ordinary skill in the art to which this invention belongs. In case of conflict, the present specification, including definitions, will control.

DETAILED DESCRIPTION OF THE INVENTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created a process for the conversion of $C_5$ sugars, and in a preferred embodiment $C_5$ sugars derived from inexpensive and abundant biomass such as lignocellulosic feed materials such as, bagasse, or corncobs to furfural and furfural derivatives. The process of the invention provides for the selective production of furfural (2-furaldehyde) and furfural derivatives from C5 sugars, e.g. obtained from biomass containing hemicellulose and cellulose. The process includes a hydrogenation process for the conversion of furfural to furfural derivatives, in particular 2-Me-THF, which 2-Me-THF is used as organic solvent in the production of the furfural. This general process can be represented schematically as shown below:

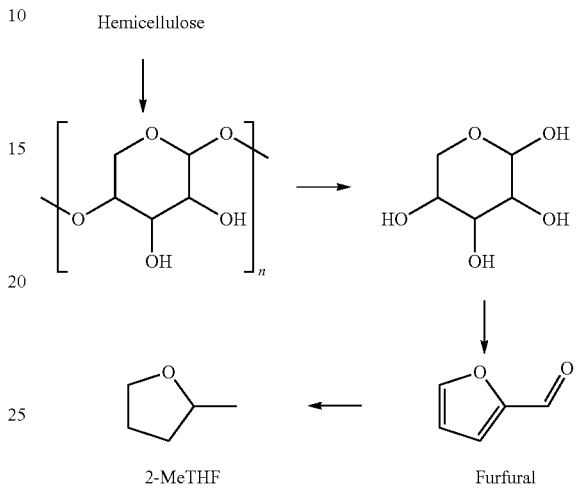

The C5 sugars may include any C5 sugar, including but not limited to xylose and arabinose and their enantiomers, but may also include isomers like xylulose. It can be provided as oligomers or polymers of C5 sugar in water soluble or insoluble form. The C5 sugars may be provided as such or dissolved in water to provide an aqueous C5 sugar-containing feed stream (step a) or may be provided as pre-existing aqueous C5 sugar-containing feed stream, depending on the origin of the C5 sugars. The aqueous C5 sugar-containing feed stream may comprise one or more C5 sugars. Preferably, the aqueous C5 sugar-containing feed stream comprises in the range of from 0.1 to 50 wt % of C5 sugar, more preferably of from 0.1 to 10 wt % of C5 sugar, even more preferably of from 0.1 to 5 wt % of C5 sugar, based on the weight of the aqueous C5 sugar-containing feed stream.

The aqueous C5 sugar-containing feed stream may be derived from any suitable source and any feedstock. Suitable feedstocks are feedstocks comprising at least one of i) a lignocellulosic feedstock containing glucan and xylan, ii) hemicellulosic material, and iii) C5 sugar monomers and C5 oligomers and polymers. In a preferred embodiment of the invention the aqueous C5 sugar-containing feed stream is derived from a biomass feedstock. The biomass material suitable for use herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste. Preferred biomass feedstocks include but are not limited to grasses, bagasse, stover, corncop, rice husk. A preferred feedstock is bagasse, more preferably bagasse comprising from about 30 wt % to about 50 wt % cellulose, from about 15 wt % to about 40 wt % hemicellulose (including xylose), from about 10 wt % to about 25 wt % total lignin (including both acid insoluble and acid soluble lignins), and an ash content ranging from about 1 wt % to about 10 wt %.

Where the aqueous $C_5$ sugar-containing feed stream is prepared from a feedstock comprising at least one of i) a lignocellulosic feedstock containing glucan and xylan, ii) hemicellulosic material, and iii) $C_5$ sugar monomers and $C_5$ oligomers and polymers, the aqueous C5 sugar-containing feed stream may be prepared providing the above mentioned feedstock (step (a1)) and contacting the feedstock with an aqueous solution to form a reaction mixture in a step (a2). The reaction mixture is subsequently heated on a step (a3) to an elevated temperature and preferably with an acid, optionally an in-situ generated acid, for a period of time sufficient to digest at least part of the feedstock and form the aqueous $C_5$ sugar-containing feed stream. In addition to the aqueous C5 sugar-containing feed steam, generally a residual, typically solid, product is formed comprising water insoluble components that were present in the feedstock, such as cellulose and lignin, and/or formed during the hydrolysis reaction (e.g. humins). Preferably, at least 10 wt %, more preferably at least 20 wt %, and even more preferably at least 30 wt %, of the feedstock is digested in step (a3). After at least part of the feedstock has been digested in step a3, the aqueous $C_5$ sugar-containing feed stream is separated from the residual product in step (a4) to provide the aqueous $C_5$ sugar-containing feed stream for the production of 2-Me-THF. The residual product may be further processed to obtain further valuable products.

The preparation of the aqueous C5 sugar-containing feed stream is further explained with reference to FIG. 1. The features described in relation to FIG. 1, however, are not limited to the embodiment of the invention shown in FIG. 1, but may also be used in combination with any other feature or embodiment of the invention as provided herein. As illustrated in the process flow diagram of FIG. 1, a process of the present disclosure may include providing a feedstock comprising at least one of i) a lignocellulosic feedstock containing glucan and xylan, ii) hemicellulosic material, and iii) $C_5$ sugar monomers and $C_5$ oligomers and polymers in the form of biomass material. The process may further include a biomass processing or preprocessing/preparation step, followed by a digestion step, and thereafter the separation of the aqueous $C_5$-sugar feed stream and the residual product.

Biomass Processing

The biomass material 11 can be used in a wet, dry or substantially dry form, and introduced directly into a digestion vessel 22 (also referred to herein as a digester), and may be pre-ground or not. For example, and biomass material used can sized by grinding to a desired particle size prior to introduction to the digester 22. In a non-limiting example, the biomass can be ground to a particle size in the range of about 0.1 mm to about 10.0 mm, about 0.1 mm to about 5.0 mm, or about 0.1 mm to about 2.0 mm. In the instance that the biomass is ground and/or sized to a specific particle size, the particle size can be selected such that the digestion process occurs with the highest efficiency.

The biomass material 11, whether ground or not, can also be mixed with water to form a slurry of a desired consistency prior to introducing the biomass to the digester 22. For example, the slurry can be in the range of from about 5 wt % solids to about 100 wt % solids by weight, e.g., about 10 wt %, about 20 wt %, about 30 wt %, about 40 wt %, about 50 wt %, about 60 wt %, about 70 wt %, about 80 wt %, about 90 wt %, or about 100 wt % solids by weight, as well as slurry concentrations within these ranges, e.g., about 25 wt % by weight, or about 5 wt % by weight.

In accordance with select aspects of the present invention, the biomass material 11 that is advanced to the digester 22 may further include or be mixed with an aqueous liquid (water) or liquids from other, downstream steps in the process. The biomass material 11 may optionally also be separated into a liquid phase and a solids phase using any suitable separation method, including centrifugation, decanting, filtration and flocculation, so as to concentrate or adjust the biomass in the initial steps of the process to optimize production.

Digestion

As shown in FIG. 1, in the next step of the production process, the biomass material 11 is introduced into a digester 22, using any suitable introducing/feeding methods, such as via a screw extruder, conveyor belt, piston or centrifugal pump, lock hopper or by way of a material addition pipe stream.

In the digestion step, the biomass is either admixed with an aqueous liquid (e.g., water) to a target solid-to-liquid (S:L) concentration, or if already in slurry form, adjusted to the appropriate concentration ratio. The solid to liquid weight ratio within the digester 22 preferably ranges from about 1:3 to 1:30, preferably about 1:3 to about 1:15, more preferably from about 1:6 to about 1:15, still more preferably from about 1:6 to about 1:10, even still more preferably from about 1:8 to about 1:10. The digestion process step is carried out at an elevated temperature, preferably above about 100° C., including in the range from about 100° C. to about 250° C., and from about 110° C. to about 160° C., for a period of time ranging from about 1 minutes to about 8 hrs, preferably from about 0.5 hrs to about 4 hrs.

The digestion step may also include the addition of one or more acids, or buffer solutions, to the digester 22 via acid stream 16, so as to adjust the pH of the digestion reaction and maintain it with a selected pH range. Preferably, the pH is less than about pH 5, more preferably less than about pH 3, and most preferably less than about pH 1. Preferably, a pH range is used in the range of from 0 to 5, more preferably of from 0 to 4, even more preferably of from 0 to 3, still more preferably of from 0 to 2. Any suitable digester equipment known in the art may be used.

In accordance with preferred aspects of the invention, the acid catalyst introduced into the digester is introduced by an acid stream 16 and is introduced in amounts and at a rate so as to optimize the digestion process. The acid catalyst is preferably an inorganic acid, most preferably a mineral acid such as HCl, $HNO_3$, $H_2SO_4$, $H_3PO_4$, $H_3BO_3$, and the like. Organic acids (e.g., acetic acid, formic acid, oxalic acid, levulinic acid, citric acid, etc.), zeolites (Si/Al from 1 to 100), acid and super-acid resins (e.g., cation exchange resin), phosphates ($NbOPO_4$, vanadium phosphate) solid silica-, silica-alumina, and titania-based supports functionalized by acid groups, and other Bronsted acids may also be used. Enzymes may also optionally be added (not shown) during the digestion step to enhance or optimize the digestion process.

In one particular example, some types of biomass that may be used as the starting material intrinsically contain acids or will form acids upon being subjected to the digestion, examples of such acids intrinsically contained or formed include, but are not limited to, formic acid or acetic acid. When using such types of biomass, the need to add acid may be reduced or even eliminated as the in-situ generated acid will provide the necessary acidic pH.

The amount of acid to be added, or the amount present within the digestion slurry, is preferably adjusted to be in the range from about 0.1 wt % to about 10 wt % acid.

Alternatively, a basic, preferably caustic pretreatment could be used instead of the acid pretreatment, this would however require a subsequent treatment to lower the pH of the aqueous C5 sugar feed stream prior to the conversion of the C5 sugar.

Separation

With continued reference to FIG. 1, once the digestion process is complete, the digestion process stream 24 is transferred to a first separator section 30, preferably a solid-liquid separator or other phase separator, where a solid product stream 31 comprising residual product is separated from the aqueous C5 sugar-containing feed stream 32 that contains primarily $C_5$-carbohydrate products, such as xylan, as a majority of the liquid product stream. The residual product may typically contain primarily cellulose or derivatives thereof and lignin. The aqueous C5 sugar-containing feed stream 32 is then fed into a reaction vessel 42 for the dehydration step. Optionally, part of stream 32 may be recycled to digester 22. This has the advantage that the C5 sugar content may be increased in steam 32.

Biphasic System

In the process according to the invention, an aqueous C5 sugar-containing feed stream, preferably prepared as described herein above, is provided as a feed to the process to produce furfural or furfural derivatives (step (a)). The aqueous $C_5$-sugar feed stream is comprised in an aqueous phase and contacted with an organic phase comprising an organic solvent, (step (b)). The aqueous phase may comprise, consist or essentially consist of the aqueous C5 sugar-containing feed stream. Preferably, aqueous phase and the organic phase when contacted form a biphasic system. Preferably, the aqueous phase and the organic phase are immiscible. The preferred organic phase for use in the present invention comprises one or more organic solvents; preferably, one or more organic solvents that are immiscible with the aqueous phase containing the $C_5$-sugars. Where the organic phase comprises two or more organic solvents, the individual organic solvents may be to some extent miscible with water, as long as the mixture of the organic solvents is essentially immiscible, i.e. form a biphasic system, with the aqueous phase. Preferably such water-immiscible organic solvents have a maximum water solubility of less than about 30 wt %, preferably less than about 10 wt %, and most preferably less than about 2 wt % at ambient (room) temperature. Preferred organic solvents include organic solvents that are tetrahydrofuranic derivatives, in particular 2-methyltetrahydrofuran.

However, the organic phase may also include other organic solvents such as 1-butanol, sec-butyl phenol (SBP), MIBK, and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), cyclic alcohols (e.g., cyclohexanol), straight or branched alkanones (e.g. butanone, pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Nitriles (such as benzonitrile), aliphatic and cycloaliphatic ethers (e.g., dichloroethylether, dimethyl ether, diethyl ether, dibutyl ether, saturated and unsaturated aliphatic or aromatic hydrocarbons (decane, toluene, benzene, cymene, 1-methyl naphthalene), other oxygenated hydrocarbons (nonyl phenol, cresol, guaiacol, anisol), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like).

Preferably, the organic solvent or the combination of organic solvents can extract 80 mol % or more of the furfural produced from the aqueous phase, while at the same time dissolve less than 1 wt %, more preferably less than 0.1 wt %, more preferably less than 0.01 wt % of water, based on the organic solvent.

It is particularly preferred that the organic phase comprises at least tetrahydrofuranic derivatives, in particular 2-methyltetrahydrofuran. An advantage of the use of tetrahydrofuranic derivatives, in particular 2-methyltetrahydrofuran, as an organic solvent in the organic phase is that tetrahydrofuranic derivatives, in particular 2-methyltetrahydrofuran, can be produced on-site from the furfural product of the process according to the invention. Reference herein to on-site produced is to tetrahydrofuranic derivatives, in particular 2-methyltetrahydrofuran that are produced as part of the process according to the invention and does not need to be imported externally. This reduces the need to provide make-up volumes of solvent externally to the process, to replace solvent losses occurring during operation of the process. The process may provide all or part of the organic solvent needs of the process during operation. In time, in-situ produced tetrahydrofuranic derivatives, in particular, 2-methyltetrahydrofuran may be used to form all of the organic solvent in the organic phase. Several tetrahydrofuranic derivatives, in particular 2-methyltetrahydrofuran are immiscible with water, while being a suitable solvent for furfural formed in step (b), and therefore is a suitable organic solvent to be used in the process according to the invention. Preferably, in the range of from 1 to 100 wt % of the organic solvent in the organic phase is a tetrahydrofuranic derivative, preferably 2-methyltetrahydrofuran, based on the weight of the organic solvent in the organic phase in step (b). More preferably, in the range of from 10 to 100 wt %, even more preferably 30 to 100 wt %, still more preferably 60 to 100 wt % of the organic solvent in the organic phase is a tetrahydrofuranic derivative, preferably 2-methyltetrahydrofuran, based on the weight of the organic solvent in the organic phase in step (b). Preferably, where the organic phase comprises more than one organic solvent including a tetrahydrofuranic derivative, preferably 2-methyltetrahydrofuran, the concentration of a tetrahydrofuranic derivative, preferably 2-methyltetrahydrofuran, increases during operation of the process, due to continuous replacement of organic solvent losses by in-situ produced tetrahydrofuranic derivative, preferably 2-methyltetrahydrofuran.

The organic phase may be contacted with the aqueous phase in any volume suitable to form a biphasic system with the aqueous phase. Preferably, the weight of the organic phase is in the range of from 5 to 95% by weight, based on the combined weight of the aqueous phase and organic phase.

Dehydration

The aqueous phase and organic phase are contacted at a temperature above about 100° C., preferably in the range of from about 100 to 300° C. to effectuate a dehydration reaction, wherein C5 sugars are dehydrated to furfural. Preferably, the aqueous phase and organic phase are contacted at a temperature in the range of from about 100° C. to about 250° C., more preferably from about 110° C. to about 200° C., and still more preferably from about 140° C. to about 180° C. The dehydration reaction may be carried out for a period of time ranging of from about 1 minute to about 24 hrs, preferably for a period of time ranging of from about 1 minute to about 12 hrs, more preferably from about 10 minutes to about 6 hours, still more preferably 30 minutes to 4 hrs., even still more preferably 30 minutes to 2 hrs. or for times within these ranges. One or more acids as described above may be added in order to catalyze the reaction process, preferably mineral acids such as $H_2SO_4$, HCl, $H_3PO_4$ and the like.

The concentration of the C5 sugars in the dehydration reactor 42 can vary depending upon the product to be obtained. However, in accordance with aspects of the present invention, it has been found that the reaction is optimized for obtaining furfural or other furan derivatives when the concentration of $C_5$ sugars in the aqueous phase is in the range of from about 0.1 to 20 wt %, more preferably of from about 0.2 to 10 wt %, based on the weight of the aqueous phase.

Due to the preference of the formed furfural to reside in the organic phase in rather than in the aqueous phase at least part of the formed furfural, and preferably more than 50 mol %, still more preferably more than 75 mol %, even still more preferably more than 80 mol % of the formed furfural will dissolve in the organic phase. The thus formed furfural-containing organic phase is subsequently separated from the aqueous phase in step (c).

The furfural in the furfural-containing organic phase may be retrieved from the process as product and may be used to prepare one or more furfural derivatives. Preferably, the process according to the invention includes converting part of the furfural produced in step (b) to one or more furfural derivatives.

Part of the furfural produced in step (b), however, is converted to a tetrahydrofuranic derivative, preferably 2-methyltetrahydrofuran. The part or all of obtained the tetrahydrofuranic derivative, preferably 2-methyltetrahydrofuran is subsequently used an organic solvent in the organic phase contacted with the aqueous phase in step (b).

Therefore, in step (d) of the process, furfural produced in step (b) is converted to a tetrahydrofuranic derivative to obtain a tetrahydrofuranic derivative-containing product. In step (e) at least part of the tetrahydrofuranic derivative in the tetrahydrofuranic derivative-containing product is provided to step (b) as organic solvent. Tetrahydrofuranic derivative, which is not provided to step (b) is preferably used for other purposes. Preferably, at least part of the tetrahydrofuranic derivative in the tetrahydrofuranic derivative-containing product is used as chemical intermediate, fuel additive, solvent.

Preferably, in step (d) at least part of the furfural is hydrogenated, preferably with an hydrogen-containing gas, in the presence of at least a first catalyst to obtain a 2-methyltetrahydrofuran-containing product. In step (e) at least part of the 2-methyltetrahydrofuran in the 2-methyltetrahydrofuran-containing product is provided to step (b) as organic solvent. The furfural may be hydrogenated in the presence of the organic solvent, preferably in the presence of 2-Me-THF, or it may be separated from the furfural-containing organic phase first. The furfural may be separated from the furfural-containing organic phase by any means, however, it is preferably separated by distillation.

The preparation of the furfural and furfural derivatives from the aqueous C5 sugar-containing feed stream is further explained in more detail with reference to FIG. 1. The features described in relation to FIG. 1, however, are not limited to the embodiment of the invention shown in FIG. 1, but may also be used in combination with any other feature or embodiment of the invention as provided herein.

Aqueous C5 sugar-containing feed stream 32 is provided to dehydration reactor 42 as an aqueous phase to a dehydration process step together with an organic solvent 43 as the organic phase. After the hydration step the dehydration product 44, i.e. the aqueous phase and furfural-comprising organic phase are provided to second separation section 45, to be separated in a C5 sugar-depleted aqueous stream 47 and a stream comprising the furfural-containing organic phase 54. Stream 54 is provided to a third separation section 50, preferably including one or more distillation steps, wherein a furfural-containing product 58, optionally containing other furan derivatives is isolated, while a residual aqueous stream 59 may be recycled back to the digestor 22, where it may serve to control the pH and the solids-to-liquids content within the digester and optimize the digestion process during a continuous loop production.

Part 58a of the furfural in the furfural-containing product is then subjected to a hydrogenation process step to yield 2-Me-THF, while the remainder 58b of the furfural in the furfural-containing product may be converted (not shown) to other products, preferably to BDO.

The dehydration of step (b) of the process according to the invention occurs in a mixture of aqueous and organic phases inside reactor 42, the aqueous phase being that carried through from the first separation section 30, the organic phase being one or more organic solvents that are substantially immiscible with the aqueous phase.

Product Recovery

Following the dehydration step, dehydration product stream 44 is transferred to a second separation section 45 to separate the aqueous phase and the organic phase. Optionally, stream 44 is treated to remove the solid byproducts, e.g. via filtration, before entering second separation section 45. The separation in step 45 may preferably be an liquid/liquid extraction step. The organic phase is separated from the aqueous phase, and the aqueous stream 47, now depleted in C5 sugars, may preferably be recycled to the digestion stage. The aqueous stream 47 may be recycled and be either fed directly back into the process at the digestion stage (not shown), or, depending upon the salt content of the aqueous stream, can undergo a further separation (not shown) to remove unwanted or excessive amounts of salts, the remaining aqueous stream being reintroduced to the digester 22 (not shown).

The furfural-containing organic phase 54, containing furfural and optionally compounds such as furfural derivatives or precursors (furan, 2-methyl THF), is then subjected to a separation in third separation section 50, preferably comprising one or more, more preferably two or more, distillation steps, wherein the furfural-containing organic phase 54 is passed through at least one distillation column to remove organic solvent(s) and residual water. Residual water 59 from the reaction that was not removed during the liquid-liquid extraction in separation step 45, and which may contain acetic acid or other water-soluble impurities, is removed from the third separation section, with recovery of furfural via furfural-containing product stream 58.

Organic solvents removed/recovered during the separation as stream 53 can be recycled back into the process, such as by reintroduction back into the dehydration reaction vessel 42, in order to minimize production costs and maintain the reaction process and reaction efficiency. Optionally, the organic solvent stream 53 can directed to a further solvent purification process (not shown) such as column distillation/separation or solvent-solvent extraction, prior to reintroduction back into the production process, so as to remove impurities, primarily humins (heavy byproducts), as well as purify the solvent before reintroduction. After the solvent purification, fresh solvent and/or fresh acid may be added to the purified solvent (not shown) prior to reintroduction to the dehydration reaction vessel 42.

Conversion of Furfural to Tetrahydrofuranic Derivatives

In step (d) of the process according to the invention, at least part of the furfural is converted to a tetrahydrofuranic derivative. This may be any tetrahyfrofuranic derivative, however preferably the tetrahydrofuranic derivative is of the general formula (1):

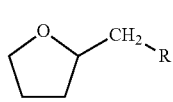

(1)

wherein:
R is selected from the group consisting of H, $C_1$-$C_5$ alkyl, —O—($C_1$-$C_5$ alkyl),

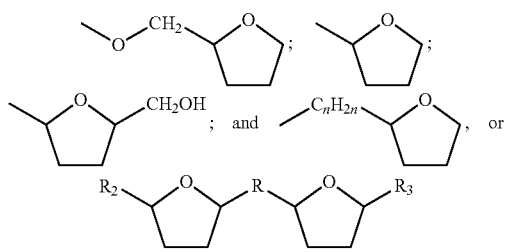

(2)

wherein:
R is a $C_1$ to $C_5$ alkyl, preferably the $C_1$-$C_5$ alkyl is methyl, ethyl, or propyl, R2 is H or $CH_3$, R3 is H or $CH_3$ and n is an integer in the range of 4 to 10.

In the process according to the invention, the furfural is preferably converted to a tetrahydrofuranic derivative by one or a combination of:
i) a hydrogenation of the furfural, optionally followed by an alkylation;
ii) an aldol-condensation; or
iii) an etherification.

The hydrogenation of the furfural in (i) herein is a carbonyl hydrogenation, i.e. hydrogenation of a —CH=O into either —$CH_2OH$ or —$CH_3$.

One or more of steps (i), (ii) or (iii) may combined with ring-hydrogenation of the furfural or its derivative. The second catalyst as described herein below may also be used for the ring-hydrogenation of the furfural or its derivative In Lange et al. (Lange et al., Furfural—A Promising Platform for Lignocellulosic Biofuels ChemSusChem 2012, 5, p 150-166), herein incorporated by reference, the conversion of furfural to tetrahydrofuranic derivatives extensively described. Examples of such conversions to tetrahydrofuranic derivatives include for instance, but are not limited to:

(v) the conversion of furfural to 2-methyltetrahydrofuran, via a gas-phase process, involving the hydrodeoxygenation to Me-furan followed by ring hydrogenation. This process is explained in more detail herein below.

(vv) the conversion of furfural to an alkyl-tetrahydrofurfuryl ether, such as ethyl-tetrahydrofurfuryl ether, via a three step process including the hydrogenation of furfural to furfuryl alcohol, followed by an acid catalysed etherification with an alcohol like ethanol, and subsequently a ring hydrogenation.

(vvv) the conversion of furfural to ditetrahydrofurfuryl ether via two-step process including the hydrogenation of furfural to furfuryl alcohol, followed by an etherification of furfuryl alcohol with mild acid and finally, ring hydrogenation.

(vvvv) the conversion of furfural to bis-tetrahydrofurfuryl alkyl, which can be done by a range of processes including but not limited to (1) a base catalysed condensation of furfural with various ketone followed by a ring-hydrogenation, eventually combined with hydrodeoxygenation of the secondary alcohol on the alkyl chain. (2) a deoxygenation of furfural to methyl furan, followed by an acid-catalyzed trimerisation of methylfuran or acid-catalyzed condensation of two methyl furan with an aldehyde and subsequently followed by a ring hydrogenation (3) an hydrogenation of furfural to furfuryl alcohol, followed by an acid catalyzed dimerisation (or oligomerization) and, finally, ring hydrogenation.

In the process according to the invention is to preferred that the furfural is converted to 2-methyl-tertrahydrofuran. Herein below, the invention is further described for the case wherein the furfural is converted to 2-methyl-tertrahydrofuran, however, the below described features apply mutatis mutandis for conversion of the furfural to other tetrahydrofuranic derivatives.

With continued reference to FIG. 1, part of the furfural obtained from the C5 sugars by the routes described above then undergoes a hydrogenation in step (d) of the process. Hydrogenation of furfural to 2-Me-THF has for instance been described in U.S. Pat. No. 8,168,807, incorporated herein by reference. The hydrogenation in the process according to the invention features a reaction bed or reactor 92 (structured or otherwise) of at least one hydrogenation catalyst (the first catalyst), and optionally a second catalyst. Following the hydrogenation, the 2-methyltetrahydrofuran-containing product can be directly isolated, or optionally passed through one or more purification steps, such as through a distillation column 100, with the distillate stream 102 comprising generally >80% pure 2-Me-THF and a further aqueous stream 104. Distillate stream 102 is, at least in part, recycled to reactor 42 as part of organic solvent 53 and/or organic solvent 43 (not shown). Preferably, the hydrogenation is performed in the presence of a hydrogen containing gas 96 provided to reactor 92. Where a hydrogen containing gas is used separation unit 100 may also separate hydrogen for an optional recycle to reactor 92.

The hydrogenation of furfural following production from C5 sugars can be performed in one or more, reactors 92. In the case of use of a plurality of reactors, the first catalyst may be disposed in a first reactor or in a first group of at least two reactors, and the bed of the optional second catalyst can be disposed in the second reactor or in the second group of at least two reactors. Preferably, the furfural or furfural-derived intermediates are contacted with the second catalyst at a lower temperature but higher hydrogen pressure compared to the temperature and pressure at which the furfuran is contacted with the first catalyst.

The furfural-containing product 58a, containing primarily furfural, preferably flows through the reactor 92 (or the reactors, only one is shown), in each case from the top downward. In the case of use of one reactor and correspondingly in the case of use of a plurality of reactors, the first catalyst is used for from 20 to 80% of the total height of the catalyst bed, preferably the upper 40 to 60% of the total height of the bed downstream of the top of the single reactor or of the first reactor 92. The remaining bed height can then optionally be formed by an optional second catalyst. When the reactor 92 or the reactors is/are flowed through from the bottom upward (envisioned but not shown), the catalyst(s) are arranged in the reverse sequence.

In the case of use of an individual reactor, such as shown in FIG. 1, and when a further, second catalyst is used, it may be advantageous to separate the part of the bed formed from the first catalyst from the part formed from the second catalyst by the introduction of an intermediate layer of inert material. Suitable intermediate separating layers are, for example, glass rings or metal rings. The hydrogenation of the furfural to the 2-Me-THF product can therefore be performed advantageously in one stage, preferably in one reactor.

In the process according to the invention, the hydrogenation in reactor 92 can be performed in the gas phase or the liquid phase, with the preference being given to working in the gas phase. In case of multiple reactors, some can be operated in gas phase while others in the liquid phase. One or more of the reactors may also be operated in the supercritical phase. In general, the process is performed in the gas phase at a temperature of from about 150° C. to about 300° C., preferably from about 170° C. to about 230° C. The pressures used are generally from 1 to 10 bar absolute, preferably from about 1 to 3 bar abs. The pressure for purposes of this application is reported as the total pressure or absolute (abs.) pressure.

As noted above, the hydrogenation reaction step 92 may optionally be performed in the liquid phase. In the liquid phase, the process according to the invention is performed generally at from about 50° C. to about 250° C. at pressures of from about 1 to about 250 bar abs., preferably at from about 20 to about 200 bar abs. Where the process is operated in two stages the second stage, i.e. ring hydrogenation, may be operated at a temperature in the range of from 20 to 400° C. and in the range of from 1 to 150 bar.

In addition to the transition metal catalyst which is required to perform the process according to the invention, and the inclusion of the optional, second catalyst, it is possible for further catalysts to be present in the reactor or in the reactors. These catalysts may serve, for example, to improve the product quality by removing impurities or converting byproducts. For example, sulfur-containing components which are generally present in a small amount in furfural can be removed by treatment with desulfurization catalysts or adsorbents based on copper and/or molybdenum oxides and/or zinc oxides.

The hydrogenation of step (d) according to the invention can be performed either continuously or batchwise, preference being given to the continuous operation of the process. In the continuous process, the amount of furfural for the hydrogenation process step is in the range from about 0.05 kg per liter (kg/L) to about 3 kg/L of catalyst per hour, more preferably from about 0.1 kg/L to about 1 kg/L of catalyst per hour.

The optional hydrogenation gases 96 used in the hydrogenation of step (d) may be any gases which comprise free hydrogen and do not comprise harmful amounts of catalyst poisons, for example CO. For example, it is possible to use reformer off-gases. Preference is given to using pure hydrogen as the hydrogenation gas. However, it is also possible additionally to use inert carrier gases such as steam or nitrogen.

Molar Hydrogen/Furfural Ratio

As seen in FIG. 1, the furfural-containing product stream 58a and the hydrogen stream 96 are introduced into the reactor 92, either separately as shown, or together as part of the same stream. The mixing ratio of hydrogen and furfural is not critical provided that sufficient amounts of hydrogen (4 equivalents) are available for the conversion of furfural to 2-methyl-THF. An excess of hydrogen is possible. In the continuous process, the hydrogen/furfural molar ratio at or near the reactor inlet (whether added separately or in a combined stream) is from about 4:1 to about 500:1, preferably from about 5:1 to about 250:1, more preferably from about 10:1 to about 100:1. In the liquid phase, the hydrogenation of step (d) can be performed in the absence or presence of a solvent or diluent, i.e., it is not necessary to perform the hydrogenation in solution. In case of multiple reactors or catalyst beds it may be desirable to provide hydrogen in a hydrogen to furfural molar ratio of 2:1 to the first reactor or catalyst bed to make methylfurfural and providing additional hydrogen between the first and second reactor or catalyst bed. The hydrogen to furfural molar ratio may be lower if an incomplete conversion and recycle of unconverted reactant is accepted.

However, it is possible to use a solvent or diluent. The solvent or diluent used may be any suitable solvent or diluent. The selection is not critical provided that the solvent or diluent used is capable of forming a homogeneous solution with the furfural to be hydrogenated.

Examples of suitable solvents or diluents include but are not limited to straight-chain or cyclic ethers, for example tetrahydrofuran or dioxane, and aliphatic alcohols in which the alkyl radical preferably has from 1 to 10 carbon atoms, especially from 3 to 6 carbon atoms. The solvent can also be an organic solvent that is recovered from the furfural production process, such as via process stream 53. In such case, furfural may not need to be fully separated from the solvent 53.

The amount of the solvent or diluent used is not particularly restricted and may be selected freely as required, although preference is given to those amounts which lead to from 10 to 70% by weight solution of the furfural intended for the hydrogenation.

Furthermore, the hydrogenation reactor, in the case of performance of the hydrogenation in the liquid phase, can be operated in straight pass, i.e. without product recycling, or in circulation, i.e. a portion of the hydrogenation mixture leaving the reactor is conducted in a circuit.

In the case of performance of the hydrogenation step of the present invention in the gas phase, the reaction products are condensed fully and removed after leaving the reactor. The gaseous fractions, hydrogen and any additional carrier gas used are returned partly to the reactor in circulation (recycle gas mode). In an exemplary preferred recycle gas mode, the ratio of recycle gas to fresh gas volumes is at least 1:1, preferably at least 5:1, more preferably at least 10:1.

Useful reactors 92 include fixed, fluidized or slurry bed reactors. The selection of the reactor type is not critical per se, provided that the catalyst arrangement in the bed, i.e. the sequence in which the reaction mixture flows through the catalysts, is not changed and that proper measures are taken to accommodate the heat of reaction. Such measures can include the use of cooling tube or coils, recycle and or inter-stage injection of cold liquid or gas. In the liquid method, it is possible to use slurry bed type reactors when the beds of the two catalyst types are arranged such that mixing of the first and second catalyst in the course of operation of the reactor is ruled out.

First Catalyst

The first, primary hydrogenation catalyst is a catalyst comprising one or more elements from Groups 2, 6-12, preferably Groups 6, 8, 9, 10, and/or 11, more preferably Group 11 of the Periodic Table of Elements (new IUPAC nomenclature), especially molybdenum, tungsten, chromium, copper, manganese, zinc, rhenium, ruthenium, and barium. As used herein, the numbering scheme for the Groups of the Periodic Table of Elements ("New IUPAC Notation") is as disclosed in Chemical and Engineering News, 63(5), 27 (1985). The total content of the aforementioned active metals is 0.5-100% by weight, preferably 15-80% by weight, calculated as the oxide. Preferably, the first catalyst comprises copper. In addition to copper, a further preferred catalyst may also comprise comprises at least one element selected from the group consisting of carbon, chromium, manganese, zinc, aluminum and barium. Suitable first catalyst include catalyst comprising copper and chromium; copper and zinc; copper, zinc and aluminum. In addition to the aforementioned metals the first catalyst may also comprise one or more promoters and/or additives, including but not limited to alkali and earth alkali metals. Useful first catalysts may include unsupported catalysts in which the catalytically active metals are present without support materials, corresponding to an active metal content of 100% by weight, as well as precipitated catalysts or supported catalysts.

Precipitated catalysts can be prepared by precipitating their catalytically active components out of their salt solutions, especially out of the solutions of their nitrates and/or acetates, for example by adding solutions of alkaline metal hydroxide and/or alkali metal carbonate and/or alkali earth metal hydroxide and/or alkaline earth metal carbonate solutions, for example as sparingly soluble hydroxides, oxide hydrates, basic salts or carbonates, then drying the resulting precipitates and converting them by calcination, generally at temperatures from about 300° C. to about 700° C., to the corresponding oxides, mixed oxides and/or mixed-valency oxides, which are then reduced by a treatment with hydrogen or with hydrogen-comprising gases at temperatures in the range from about 50° C. to about 700° C. to the metals in question and/or oxidic compounds of lower oxidation state and converted to the actual, catalytically active form. In general, reduction is continued until no further water is formed. In the preparation of precipitated catalysts which comprise a support material, the catalytically active components can be precipitated in the presence of the support material in question. The catalytically active components may advantageously, though, also be precipitated simultaneously with the support material from the salt solutions in question. In accordance with processes according to select aspects of the present invention, preference is given to using hydrogenation catalysts which comprise metals or metal compounds which catalyze the hydrogenation deposited on a support material.

Apart from the abovementioned precipitated catalysts which, apart from the catalytically active components, also additionally comprise a support material, suitable catalysts for the process according to the invention are generally also supported catalysts, in which the components having catalytically hydrogenating action have been applied to a support material, for example by impregnation.

The way in which the catalytically active metals are applied to the support is generally not critical and it can be accomplished in various ways. The catalytically active metals can be applied to the support materials, for example, by impregnation with solutions or suspensions of the salts or oxides of the elements in question, drying and subsequent reduction of the metal compounds to give the metals or compounds of lower oxidation state in question by means of a reducing agent, preferably with hydrogen or complex hydrides. Another means of applying the catalytically active metals to these supports consists in impregnating the supports with solutions of thermally readily decomposable salts, for example with nitrates, or thermally readily decomposable complexes, for example carbonyl or hydride complexes of the catalytically active metals, and heating the impregnated supports thus obtained to temperatures of from 300° C. to 600° C. for the purpose of thermal decomposition of the adsorbed metal compounds. This thermal decomposition is preferably undertaken under a protective gas atmosphere. Suitable protective gases are, for example, nitrogen, carbon dioxide, hydrogen or the noble gases. In addition, the catalytically active metals can be deposited on the catalyst support by vapor deposition or by flame-spraying. The content in these supported catalysts of the catalytically active metals is in principle not critical for the success of the process according to the invention. However, higher contents of catalytically active metals generally lead to higher space-time yields than lower contents.

In general, supported catalysts whose content of catalytically active metals, calculated as the oxide, is from 0.5 to 90% by weight, preferably from 15 to 80% by weight, based on the overall catalyst, are used. Since these content data are based on the overall catalyst including support material, but the different support materials have very different specific weights and specific surface areas, the contents may also be lower or higher than these data, without this having a disadvantageous effect on the result of the process according to the invention. It will be appreciated that it is also possible for a plurality of the catalytically active metals to be applied on the particular support material.

Both the precipitated catalysts and supported catalysts can also be activated in situ at the start of the reaction by the hydrogen present, but these catalysts are preferably activated separately before they are used.

The support materials used may generally be the oxides of aluminum, zirconium dioxide, silicon dioxide, magnesium and calcium oxide. It will be appreciated that mixtures of different support materials may also serve as the support for heterogeneous catalysts useable in the process according to the invention.

Second/Additional Catalysts

As indicated above, the reactor(s) 92 may optionally include a second hydrogenation catalyst in order to affect the efficiency and hydrogenation rate of the reaction. The second catalyst used in accordance with the invention preferably has, as an active metal, at least one metal from groups 8, 9, and 10 of the periodic table of the elements, especially nickel, ruthenium, rhodium, iridium, gold, palladium and/or platinum, preferably palladium and/or platinum. A preferred second catalyst is a second catalyst that comprises nickel. The second catalyst may additionally comprise one or more metals from groups 1 to 7 and 11 to 15, preferably groups 1, 2, 4, 7, 11 and 12 of the periodic table of the elements. The elements of groups 1 and 2 of the periodic table of the elements, when included in the second catalyst composition, are preferably sodium, potassium, calcium or magnesium. The second catalyst is preferably a supported catalyst.

The application of the active metals can be achieved by impregnating the support in aqueous metal salt solutions, for example aqueous palladium salt solutions, by spraying corresponding metal salt solutions onto the support or by other suitable processes. Suitable metal salts of platinum and palladium are the nitrates, nitrosylnitrates, halides, carbonates, carboxylates, acetylacetonates, chlorides, chloro complexes or amine complexes of the corresponding metals, preference being given to the nitrates.

The supports coated or impregnated with the metal salt solution are subsequently dried, preferably at temperatures between about 100° C. and about 150° C., and optionally calcined at temperatures between about 200° C. and about 600° C. In the case of separate impregnation, the catalyst can be dried after each impregnation step and optionally calcined as described above. The sequence in which the active components are applied by impregnation is freely selectable, and known to those of skill in the art.

The metal salt solution or solutions may be applied to the support or supports in such an amount that the total content of active metal, based in each case of the total weight of the catalyst, is from about 0.1 to about 30% by weight, preferably from about 0.1 to about 10% by weight, more preferably from about 0.25 to about 5% by weight.

Useable support metals include, but are not limited to, carbon, aluminum oxide, silicon dioxide, silicon carbide, calcium oxide, titanium dioxide and/or zirconium dioxide or mixtures thereof, preference being given to using carbon.
Cellulosic Residue The residual product 31 may be further processed prepare further valuable products (not shown). Typically, the residual product 31 contains C6 sugars or its derivative, oligomer and polymers. The residual product can be sent to a hydrolysis step, followed by a fermentation step to yield one or more commercially important alcohol or acid products. The C6 containing residue may also be processed using chemo-catalysis to produce various valuable intermediates such as HMF, levulinic acid, C6 sugar alcohols, short alcohols, diols, polyols, ketones and aldehydes and the derivative thereof in pure or mixed form.

Other and further embodiments utilizing one or more aspects of the inventions described above can be devised without departing from the spirit of Applicant's invention. For example, two or more catalysts can be used, separately or in combination, in one or more reactors, in one or more stages. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

EXAMPLES

The invention is illustrated by the following non-limiting examples.

Example 1

Furfural Selectivity Using the Furfural Derived Solvent Methyl Tetrahydrofuran (MeTHF) as an Extracting Solvent for Furfural Production 100 g of 5 wt % xylose solution (which is used as a model feed for a feed prepared by the digestion of a biomass feedstock) was prepared along with 1 wt % $H_2SO_4$ acid concentration and was provided to a reactor. An equal amount (100 g) of Methyl Tetrahydrofuran (MeTHF) was added to the reactor as extracting organic solvent to create a biphasic reaction medium. The reactor was then heated to 170° C. and the reaction was allowed to proceed for 1 hour. After the reaction was completed the reactor was cooled to room temperature and the two liquid phases were separated. The aqueous layer was analyzed using High Pressure Liquid Chromatography (HPLC) and organic layer was analyzed using Gas Chromatography (GC) to determine the composition. The aqueous layer was analyzed and quantified for unconverted xylose and furfural using HPLC system (Shimadzu) equipped with a refractive index detector (Shimadzu) on a BIO-RAD 87H Column. Prior to injection, the samples were filtered through 0.45 μm HV filters (Millipore, Bedford, Mass., USA), and a volume of 10 μL was injected. The mobile phase for the column was 5 mM $H_2SO_4$ in Milli-Q water at a flow rate of 0.6 mL/min. The furfural concentration in the organic phase or layer was measured using GC. Agilent 6890 GC with a DB-1301 capillary column installed in its split/splitless inlet was used with the FID (Oven Temp Program—40° C., Hold 3 min, Ramp 10° C./min to 280° C. Hold 3 min). The column parameters were 30 m length, 0.25 mm ID, and 1.0 μm film thickness. As a result of this run, almost 99% of xylose was converted with 60% selectivity towards furfural. This example successfully demonstrates use of furfural derived solvent such as MeTHF as an extracting solvent for use in furfural production.

That which is claimed is:
1. A process for preparing furfural and/or furfural derivatives, comprising:
(a) providing an aqueous $C_5$ sugar-containing feed stream;
(b) contacting an aqueous phase comprising the aqueous $C_5$ sugar-containing feed stream with an organic phase comprising organic solvent at a temperature in the range of about 100° C. to about 300° C. for a time sufficient to effect a dehydration reaction to convert $C_5$ sugar to furfural, wherein at least part of the furfural dissolves in the organic solvent phase to form a furfural-containing organic phase;
(c) separating the furfural-containing organic phase from the aqueous phase;
(d) separating furfural from the furfural-containing organic phase;
(e) converting at least part of the furfural to a tetrahydrofuranic derivative to obtain tetrahydrofuranic derivative-containing product; and
(f) providing at least part of the tetrahydrofuranic derivative to step (b) as organic solvent.

2. The process of claim 1, wherein the tetrahydrofuranic derivative is of the general formula (1):

wherein:
R is selected from the group consisting of H, $C_1$-$C_5$ alkyl, —O—($C_1$-$C_5$ alkyl),

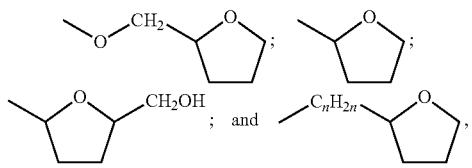

or
wherein the tetrahydrofuranic derivative is of the general formula (2):

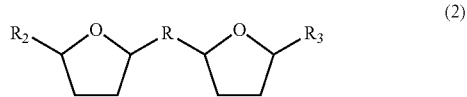

wherein:
R is a $C_1$ to $C_5$ alkyl, R2 is H or $CH_3$, R3 is H or $CH_3$ and n is an integer in the range of 4 to 10.

3. The process of claim, wherein the furfural is converted to a tetrahydrofuranic derivative by one or a combination of:
i) a hydrogenation of the furfural, optionally followed by an alkylation;
ii) an aldol-condensation; or
iii) an etherification.

4. The process of claim 1, wherein the furfural is converted to 2-methyltetrahydrofuran by hydrogenating part of the furfural in the presence of a reactor bed comprising at least a first catalyst to obtain 2-methyltetrahydrofuran-containing product; and wherein in step (e) a least part of the 2-methyltetrahydrofuran is provided to step (b) as organic solvent.

5. The process of claim 4, wherein the hydrogenation is carried out in one stage.

6. The process of claim 4, wherein the first catalyst comprises copper.

7. The process of claim 4, wherein the first catalyst further comprises at least one element selected from the group consisting of chromium, manganese, zinc, aluminum and barium.

8. The process of claim 4, further comprising a second catalyst in the hydrogenating step, the second catalyst comprising at least one element selected from the group consisting of group 8 metals, group 9 metals and group 10 metals of the periodic table.

9. The process of claim 8, wherein the second catalyst comprises nickel.

10. The process of claim 8, wherein the second catalyst further comprises at least one element of the periodic table selected from the group consisting of a group 1 to 7 and group 11 to 15.

11. The process of claim 4, wherein the first catalyst and optionally the second catalyst is supported on a support material comprising at least one material selected form the group consisting of activated carbon, aluminum oxide, silicon dioxide, silicon carbide, calcium oxide, titanium dioxide, and zirconium dioxide.

12. The process of claim 4, further comprising in step (e), wherein at least part of the 2-methyltetrahydrofuran-containing product is condensed to obtain a first phase having a water content of at least about 90% by weight and a second phase having a 2-methyltetrahydrofuran content of at least about 80% by weight and at least part of the second phase is provided as organic solvent to step (b).

13. The process of claim 4, wherein the hydrogenation in step (d) is performed in the presence of a 2-methyltetrahydrofuran derivative.

14. The process of claim 1, wherein in the range of from 1 to 100 wt % of the organic solvent organic phase in step (b) is a tetrahydrofuranic derivative.

15. The process of claim 1, wherein the aqueous $C_5$ sugar-containing feed stream is prepared by:
(a1) providing a feedstock comprising at least one of i) a lignocellulosic feedstock containing glucan and xylan, ii) hemicellulosic material, and iii) $C_5$ sugar monomers, $C_5$ oligomers and $C_5$ polymers;
(a2) contacting the feedstock with an aqueous medium to form a reaction mixture;
(a3) heating the reaction mixture to an elevated temperature with at least one acid for a period of time sufficient to digest at least part the feedstock and form the aqueous $C_5$ sugar-containing feed stream and a residual product; and
(a4) separating the aqueous $C_5$ sugar-containing feed stream from the residual product.

16. The process of claim 1, wherein at least part of the tetrahydrofuranic derivative in the tetrahydrofuranic derivative-containing product is used as a chemical intermediate, fuel additive, or solvent.

17. The process of claim 1, wherein the organic phase comprises at least one water-immiscible organic solvent.

* * * * *